(12) United States Patent
Lauderdale

(10) Patent No.: US 7,205,281 B2
(45) Date of Patent: Apr. 17, 2007

(54) PROCESS FOR THE SYNCHRONIZATION OF OVULATION FOR TIMED BREEDING WITHOUT HEAT DETECTION

(75) Inventor: James W. Lauderdale, Augusta, MI (US)

(73) Assignee: Thorn BioScience, LLC, Louisville, KY (US)

( * ) Notice: Subject to any disclaimer, the term of this patent is extended or adjusted under 35 U.S.C. 154(b) by 0 days.

(21) Appl. No.: 10/954,314

(22) Filed: Sep. 30, 2004

(65) Prior Publication Data

US 2005/0130894 A1 Jun. 16, 2005

Related U.S. Application Data

(60) Provisional application No. 60/508,509, filed on Oct. 3, 2003.

(51) Int. Cl.
*A61K 38/00* (2006.01)
*A61K 38/24* (2006.01)
*A01N 37/00* (2006.01)

(52) U.S. Cl. .................. 514/12; 514/2; 514/8
(58) Field of Classification Search .............. None
See application file for complete search history.

(56) References Cited

U.S. PATENT DOCUMENTS

| | | |
|---|---|---|
| 3,860,701 A | 1/1975 | Short |
| 3,991,750 A | 11/1976 | Vickery |
| 4,732,763 A | 3/1988 | Beck et al. |
| 4,756,907 A | 7/1988 | Beck et al. |
| 4,780,451 A | 10/1988 | Donaldson |
| 4,975,280 A | 12/1990 | Schacht et al. |
| 5,180,711 A | 1/1993 | Hodgen |
| 5,418,228 A | 5/1995 | Bennink |
| 5,434,146 A | 7/1995 | Labrie et al. |
| 5,512,303 A | 4/1996 | Garza Flores et al. |
| 5,585,370 A | 12/1996 | Casper |
| 5,589,457 A | 12/1996 | Wiltbank |
| 5,605,702 A | 2/1997 | Teillaud et al. |
| 5,633,014 A | 5/1997 | Garza Flores et al. |
| 5,650,173 A | 7/1997 | Ramstack et al. |
| 5,686,097 A | 11/1997 | Taskovich et al. |
| 5,747,058 A | 5/1998 | Tipton et al. |
| 6,028,057 A | 2/2000 | Burns |
| 6,051,558 A | 4/2000 | Burns et al. |

FOREIGN PATENT DOCUMENTS

| | | |
|---|---|---|
| GB | 2 166 951 | 5/1986 |
| WO | WO 97/32572 | 9/1997 |
| WO | WO 98/53837 | 12/1998 |

OTHER PUBLICATIONS

Ramakrishnappa et al., Anim Reprod Sci. 2005; 88: 95-113.*
Wähner and Hühn, Reprod Dom Anim. 1996; 31: 477-482.*

Barb, et al., "Evaluation of the saber delivery system for the controlled release of deslorelin: Effect of dose in estrogen primed ovarectomized gilts" *Proceed. Int'l. Symp. Control. Rel. Bioact. Mater.*, 26: 1170-1171 (1999).

Betteridge and Raeside, "Observation of the ovary by peritoneal cannulation in pigs" *Res. Vet. Sci.* 3:390-398 (1962).

Britt, et al., "Induction of fertile estrus in prepuberal gilts by treatment with a combination of pregnant mare's serum gonadotrophin and human chorionic gonadotropin," *J. Anim. Sci.* 67:1148-53 (1989).

Brussow et al, "Control of ovulation with a GnRH analog in gilts and sows" *Theriogenology* 46: 925-934 (1996).

Burns and Douglas, "Effects of daily administration of estradiol-17β on follicular growth, ovulation, and plasma hormoes in mares" *Biology of Reproduction* 24: 1026-1031 (1981).

Burns, et al., "Evaluation of biodegradable microspheres for the controlled release of progesterone and estrodiol in an ovulation control program for cycling mares," *J. Equine Vet. Sci.* 13(9):521-24 (1993).

Cook, et al., "Effects of exogenous estradiol treatment in cyclic mares following PGF induced luteal regression" *Proceeding of the 13th Equine Nutrition & Physiology Symposium* 370-374.

De Rensis et al., "Fertility of sows following artificial insemination at a gonadotrophin-induced estrus coincident with weaning" *Animal Reproduction Science* 76: 245-250 (2003).

Donbrow, ed., "Microcapsules and Nanoparticles in Medicine and Pharmacy," (CRC Press, Boca Raton 1992) (Table of Contents Only).

Du Mesnil, et al., "Reporductive physiology and artificial insemination in pigs" J.P. *Vet. Rec.* 87: 562-568 (1970).

Flowers and Alhusen, "Reproductive performance and estimates of labor requirements associated with combinations of artificial insemination and naturall service in swine" *J. Animal Science* 70:615-621 (1992).

Geisert, et al., "Length of pseudopregnancy and pattern of uterine release as influenced by time and duration of estrogen administration in the pig," *J. Reprod. Fert.* 79:163-72 (1987).

Gerrits et al., "Effect of synchronization of estrus on fertility in gilts" *J. Animal Sci.* 21: 1022 (1962).

(Continued)

*Primary Examiner*—Elizabeth Kemmerer
*Assistant Examiner*—Christina Borgeest
(74) *Attorney, Agent, or Firm*—Pabst Patent Group LLP

(57) ABSTRACT

A method for synchronizing ovulation in sows and gilts by a single injection of hormones is disclosed. A hormone, gonadotropin releasing hormone (GnRH), luteinizing hormone (LH), follicle stimulating hormone (FSH), human chorionic gonadotropin (hCG), analogues, derivatives, agonists or combinations thereof is administered to an open sow post weaning at a specific time to stimulate ovulation of mature responsive follicles. The sow is then bred, without heat detection, at a specific subsequent timed interval after injection with hormone, with one or two artificial or natural breedings. In gilts, the hormone is injected at a timed interval from onset of estrus or at a specific timed interval following Prostaglandin F2a for those gilts which have been held in a state of pseudopregnancy.

15 Claims, 1 Drawing Sheet

OTHER PUBLICATIONS

Guthrie, et al., "Treatment of pregnant gilts with a prostaglandin analogue, Cloprostenol, to control estrus and fertility," *J. Reprod. Fert.* 52:271-73 (1978).

Guthrie, et al., Changes in plasma estrogen, luteinizing hormone, follicle-stimulating hormone and 13,14-dihydro-15-keto-prostaglandin $F_2$ during blockade of luteolysis in pigs after human. Hansel et al., "Corpora lutea of the large domestic animals" *Biology of Reproduction* 8: 222 (1973).

Hodson et al., "Effect of gonadotropin dose and postpartum status on induced ovulation and pregnancy in lactating sows" *J. Animal Science* 52(4): 688-695 (1981).

Howard, et al., "Prostaglandin $F_2$ causes regression of an hCG-induced corpus luteum before Day 5 of its lifespan in cattle," *J. Reprod. Fert.* 90:245-53 (1990).

Hunter and Polge, "Maturation of follicular oocytes in the pig after injection of human chorionic gonadotrophin" *J. Repro. Fert.* 12: 525-531 (1966).

Hunter, "Physiological factors influencing ovulation, fertilization, early embryonic development and establishment of pregnancy in pigs" *Brit. Vet. J.* 133: 461-470 (1977).

Hurtgen and Leman, "Seasonal influence on the fertility of sows and gilts" *J. Amer. Vet. Med. Ass.* 177: 631-635 (1980).

Jackson and Hutchinson, "Slow release formulations of prostaglandin and luteolysis in the pig" *Veterinary Record* 106: 33-34 (1980).

Martinat-Botte et al., "Control of pig reproduction in a breeding programme" *J. Reprod. Fert. Suppl.* 33: 211-228 (1985).

Niswender et al., "Radioimmunoassay of serum levels of luteinizing hormone throughout the estrous cycle in pigs" *Endocrinology* 37: 576-580 (1970).

Peters et al., "Effect of gonadotrophin-releasing hormone on the fertility of sows kept outdoors" *Vet. Record* 147:649-652 (2000).

Polge et al., "Synchronisation of ovulation and artificial insemination in pigs" *Veterinary Record* 83, 136-142 (1968).

Prokofeva, "Composition for oestrus cycle control in sows-containing hydroxyl-progesterone caproate, oestradiol valerate, oil, and benzyl benzoate to improve heat synchronization" *Derwent Publications, Limited* SU-549118 (1977). (Abstract only).

Pusateri, et al. "Maternal Recognition of Pregnancy in Swine. I. Minimal Requirement for Exogenous Estradiol-17 to Induce Either Short or Long Pseudopregnancy in Cycling Gilts," *Biol. Reproduction* 55:582-89 (1996).

Sechin et al., "Effect of equine chorionic gonadotropin on weaning to first service interval and litter size of female swine" *Theriogenology* 51:1175-1182 (1999).

Sheffield, et al., "Effect of estradiol and relaxin on collagen and non-collagen protein synthesis by mammary fibroblasts," *Life Sci.* 35(22):2199-203 (1984).

Soede, N.M. and Kemp, "In synchronized pigs, the duration of ovulation is not affected by insemination and is not a determinant for early embryonic diversity" B. *Theriogenology* 39: 1043-1053 (1993).

Stevenson, et al., "Role of the Ovary in Controlling Luteinizing Hormone, Follicle Stimulating Hormone, and Prolactin Secretion During and After Lactation in Pigs," *Biol. Reproduction* 24:341-53 (1981).

Stork, M.G., "Seasonal reproductive inefficiency in large pig breeding units in Briain" *Veterinary Record* 104: 49-52 (1979).

Tilton, et al., "Evaluation of Response to Hormonal Therapy in Prepubertal Gilts of Different Genetic Lines," *J. Anim. Sci.* 73:3062-68 (1995).

Ulberg et al, "The effects of progesterone upon ovarian function in gilts" *J. Animal Sci.* 10: 665-671 (1951).

Van Der Meulen, et al., "Effect of intra-uterine oestradiol-17β administration of inter-oestrous interval in the pig" *Animal Reproduction Science* 24: 305-313 (1991).

* cited by examiner

PROCESS FOR THE SYNCHRONIZATION OF OVULATION FOR TIMED BREEDING WITHOUT HEAT DETECTION

CROSS-REFERENCE TO RELATED APPLICATIONS

This application claims priority to U.S. Ser. No. 60/508,509 filed Oct. 3, 2003 entitled "Process for the Synchronization of Ovulation for Timed Breeding Without Heat Detection" by James W. Lauderdale.

FIELD OF THE INVENTION

This invention relates to the reproductive management of sows and gilts and more particularly processes for synchronizing ovulation in such swine for timed artificial breeding with a reduction in or with no regard to estrus detection.

BACKGROUND OF THE INVENTION

The administration of hormones to control the reproductive process in domestic animals such as horse, cows, sheep, goats and swine is well known in the art. One approach to managing reproductive processes in domestic mammals involves the direct administration of gonadotropins to domestic animals. Gonadotropins are produced by the anterior lobe of the pituitary gland and are characterized as follicle stimulating hormone (FSH) and luteinizing hormone (LH). Typically such hormones are extracted from the porcine pituitary glands and are administered to domestic animals to control or stimulate the ovulatory process. One gonadotropin formulation is FSH-P produced by Schering-Plough Corp. FSH-P has a fairly high and variable content of luteinizing hormone and while effective in producing an ovulatory response, has been less than desirable in producing high fertilization rates and viable embryos. Another formulation, which contains a low and controlled level of luteinizing hormone with high follicle stimulating activity, is disclosed in U.S. Pat. No. B1 4,780,451 to Donaldson. Gonadotropin release hormone (GnRH) can also be used to stimulate ovulation as related in U.S. Pat. No. 5,180,711 to Hodgen. In that instance GnRH is administered subsequent to a GnRH antagonist which effectively suppressed natural gonadotropin levels. The GnRH then stimulates the release of endogenous FSH and LH leading to follicle development and ovulation. The use of similar hormones for control of ovulation in cattle is described in U.S. Pat. No. 5,589,457 to Wiltbank.

A number of different preparations of gonadotropins are available commercially including Fertagyl, Cystorelin, Chorulon, Folltropin-V, Factrel, PG600, Receptal and others. In addition, certain GnRH analogs, or agonists, such as deslorelin and buserelin are also available. These hormones may be administered to the various domestic species by implant, by intramuscular or subcutaneous injection or by mucosal applications such as intranasal and intravaginal routes. Gonadotropins may also be administered with excipients or delivery systems, which delay or control the release over time to produce more natural or even extended release patterns of LH. See U.S. Pat. No. 6,051,558 to Burns, et. al.

A major goal of commercial swine production is to maximize reproductive efficiency. Increased reproductive efficiency offers producers substantial opportunities to reduce production costs and enhance profitability. Part of the production costs is the result of a heavy reliance on daily heat detection of individual animals (W. L. Flowers and H.-D. Alhusen, (1992) J. Animal Science 70:615–621) since gilts and sows are bred based on spontaneous estrus cycles. Approximately half of the labor in swine breeding facilities is devoted to detection of estrus in breeding gilts and sows. Gilts or sows must be checked at least once daily in order to be bred at the correct time, and, if artificial insemination ("AI") is used, it may be necessary to check twice daily in order to achieve the best results. Rigorous heat detection is necessary because it is difficult to predict the day of heat for any cyclic gilt or open sow, even with good heat detection records.

It is therefore an object of the present invention to provide a means of inducing ovulation that allows for artificial insemination in the absence of heat detection.

SUMMARY OF THE INVENTION

A method for synchronizing ovulation in swine in order to provide for effective reproductive management through timed artificial insemination without estrus (heat) detection has been developed. A hormone, gonadotropin releasing hormone (GnRH), luteinizing hormone (LH), follicle stimulating hormone (FSH), human chorionic gonadotropin (hCG) or a combination drug with similar activity such as PG600, is administered to a postpartum sow at a timed interval post weaning in order to stimulate ovulation. After a suitable period of time (according to breed of swine and farrowing records), a single timed AI breeding is administered to achieve normal pregnancy rates and litter sizes with no regard to estrus detection.

Preferably the GnRH is administered in the form of 50 mcg of deslorelin in an extended release carrier such as the SAIB excipient available from Birmingham Polymers. Other GnRH preparations may be administered in the range of 10–100 mcg. Such products as hCG may be administered in doses as high as 750 IU. The dose amounts as designated herein are for the hormones in their "native form" or in the case of GnRH analogs, such as deslorelin, are designated as the equivalent amount of the hormone in question in the "native form."

Examples demonstrate that the method of synchronization was highly effective as compared to controls requiring much more labor intensive breeding techniques.

DETAILED DESCRIPTION OF THE INVENTION

Figure 1A:
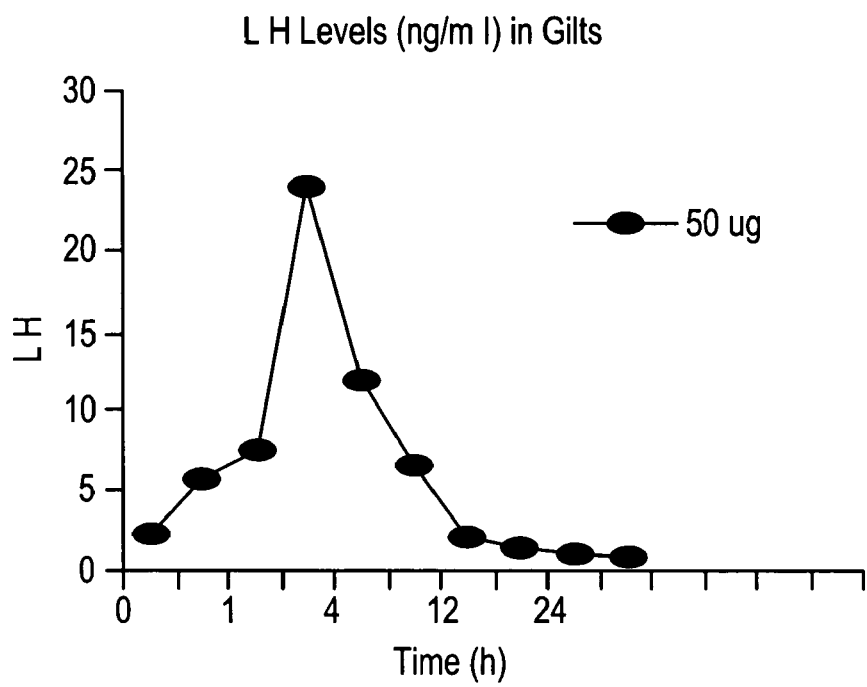
FIGS. 1a and 1b are graphs showing that a single injection of 50 mcg of deslorelin in SAIB produced a LH peak about twice normal value (FIG. 1a), compared to Hansel et al., (1973) Biology of Reproduction 8, 222) (FIG. 1b), which returned to base level by 18 hours as determined by RIA.

Effective reproductive management of swine has become an important factor for swine producers, particularly in view of continued vertical integration of the industry where the predominant model is an "all-in-all-out" method of production. In this method waves of pigs are produced for cost efficiencies, disease control and feed rationing to produce groups of pigs meeting ideal marketing weights at the same time. Reproductive control is the first step in the process whereby farrowing houses are filled with gilts and/or sows which are bred to farrow during a tight interval, usually 5 to 7 days. This assures that weaning of piglets from the whole farrowing house can occur on the same day and in turn groups of pigs from any one unit are of the same age, close in size and stage of development. In commercial swine husbandry this helps control disease, reduces stress among aggregated groups and maximizes the utilization of various feed formulations as the pigs proceed toward market weight.

It is well known by those skilled in the art of swine production that to maximize reproductive efficiency estrus detection becomes an important and major task. Estrus is the period of boar or breeding receptivity. Estrus detection, as presently practiced on commercial swine farms, is a daily or twice daily labor-intensive process. The process involves individual exposure of each gilt or sow to a boar and manually putting back-pressure (the "riding test") on each animal to determine if the standing heat "immobilization" reflex is triggered (Gordon, I., Controlled Reproduction in Pigs, CAB International, 1997). This is performed on each individual in the breeding pool not known to have been recently bred and gone out of estrus. The process continues right through the estrus period and the sow or gilt is bred multiple times until it no longer is deemed receptive.

At the start of a normal estrus (heat) in domestic animals, the brain secretes large amounts of GnRH that in turn causes a release of follicle stimulating hormone and luteinizing hormone (LH) which will cause ovulation of the Graafian follicles over a 24–48 hour time period. In swine, peak estradiol levels occur several days prior to the signs of estrus and, indeed, the LH peak often occurs at the time estrus is evidenced (Niswender et al Endocrinology 37, 576–580 (1970)).

The duration of the estrus cycle in the sow is relatively constant year round at 21 days without obvious seasonality (Asdell, (1964) Patterns of Mammalian Reproduction, 2nd edn. Cornell University Press, Ithaca, USA, pp. 670; Dziuk, (1991) Reproduction in the pig. In: Cupps, P. T. (ed.) Reproduction in Domestic Animals, 4th edn. Academic Press, New York, pp. 471–489) although there may be some tendency for less consistency in late summer (Stork, M. G. (1979) Veterinary Record 104, 49≠52; Hurtgen and Leman, (1980) J. Amer. Vet. Med. Ass. 177, 631–635) possibly due to shortened day length. Gilts may tend toward shorter cycles than mature sows (Asdell, (1964) Patterns of Mammalian Reproduction, 2nd edn. Cornell University Press, Ithaca, USA, 670 pp.). Behavioral estrus occurs over a 2–3 day period, the onset of which is preceded by peak estradiol levels and coincides with peak LH levels (Hansel et al., (1973) Biol. Repro. 8, 222) which are responsible for the maturation and ovulation of follicles (Hunter and Polge, (1966) J. Repro. Fert. 12, 525–531; Hunter (1977) Brit. Vet. J. 133, 499–501). Ovulation occurs about 40 hours after the onset of estrus if estrus is 2 days in duration or about 75% of the way through the estrus if it is longer than 2 days (Gordon, 1997 Controlled Reproduction in Pigs, CAB International, 1997). The multiple ovulations occur over approximately 1–6 hours (Betteridge and Raeside, (1962) Res. Vet. Sci. 3, 390–398; Du Mesnil du Buisson and Signoret, 1970 Du Mesnil du Boisson, F. and Signoret, J. P. (1970) Vet. Rec. 87, 562–568; Soede and Kemp, 1993 Soede, N. M. and Kemp, B. (1993) Theriogenology 39, 1043–1053).

Attempted hormonal control of the estrus period and ovulation is well described in the literature. The controls have been described using more than one steroid/gonadotropin/prostaglandin or their analogs in series or combination of injections at various timings depending on the nature of the particular group, including pre-pubertal and pubertal gilts, sows farrowed but pre-weaning, at the time of weaning or post weaning. Injectable and oral progesterone and progestagens (Ulberg et al (1951) J. Animal Sci. 10, 665–671); Gerrits et al., (1963) J. Animal Sci. 21, 1022–1025), altrenogest (Martinat-Botte et al., 1985 Martinatt-Botte, F., Bariteau, F., Badouard, B. and Terqui, M. (1985) J. Reprod. Fert. Suppl. 33, 211–228) altrenogest with PMSG and GnRH/hCG (Busch et al., (1992) Monatshefte fur Veteriarmedizin 47, 307–316), prostaglandins (Jackson and Hutchinson, Veterinary Record 106 33–34), methallibure, PMSG and hCG (Polge et al., (1968) Veterinary Record 83, 136–142; F. De Rensis et al., (2003) Animal Reproduction Science 76: 245–250) have either met with limited success (progestagens), failed (prostaglandins), been banned from the market (methallibure) or require daily oral dosing (altrenogest), multiple injections (estradiol, progesterone) or combinations of drugs (PMSG, hCG GnRH) coupled with continued heat detection in order to create detectable breeding efficiencies.

Those skilled in the art continue to use multiple sequential hormonal intervention in order to control the time of estrus and time of ovulation in the estrous cycling gilt, such as a sequence of altrenogest or methallibure to inhibit pituitary gonadotropin followed by eCG or hCG or a GnRH, and postpartum sow, such as eCG post-weaning followed by a GnRH or a combination of a GnRH and hCG with breeding by a timed AI (Brussow et al, (1996) Theriogenology 46: 925–934). GnRH has been investigated as a "fertility enhancer" in the sow by injecting 1 day or 11 to 12 days following first service (Peters et al, (2000) Vet. Record 147:649–652). As recently as 2003 (DeRensis et al, 2003), those skilled in the art continued to investigate PG 600 injected at or prior to weaning as a method to shorten the wean to estrus interval but not for timed ovulation for timed breeding. Recent reviews of the hormonal methods to control estrus and breeding of estrous cyclic gilts and postpartum sows continue to cite processes as identified above (Kirkwood, (1999) Swine Health Prod. 7(1):29–35; Day, et al. Control of reproduction in the female pig. 30$^{th}$ Annual Meeting, American Association of Swine Practitioners, Workshop #6, St. Louis, Mo. Feb. 27, 1999, pp. 23–39). The scientific literature from the early 1960s through 2003 reports the requirement for either multiple sequential hormonal treatments in estrous cycling gilts or the use of various combinations of or single use of gonadotropins for attempting to manage the time of estrus in postpartum sows. No one skilled in the art has reported on a single injection of a GnRH postpartum followed by one or two timed breedings resulting in normal fertility in the absence of estrus detection and breeding associated with the detected estrus.

The ultimate goal of synchronizing estrus and/or ovulation, reducing post weaning to estrus intervals or breeding gilts as replacements is to keep the farrowing houses full and grouped for all-in-all-out production. Meanwhile, all breeding management programs utilize standard heat detection methods throughout the early detection and estrus period until breeding is complete and the gilt or sow is no longer receptive.

There is a wealth of information indicating that hormonal induction of estrus post weaning with individual gonadotropins or with a combination drug such as PG600 is efficacious in producing a fertile estrus after weaning (Kirkwood, R. N. (1999) Swine Health Prod. 7(1):29–35; Sechin et al., (1999) Theriogenology 51:1175–1182). However, F. De Rensis et al. state that while injection of gonadotropins at weaning will produce an earlier fertile estrus, by inducing an earlier estrus the time between onset of estrus and ovulation increases, making prediction of ovulation even more difficult (Knox et al. (2001) J. Animal Sci. 79:796–802). Furthermore, the research has demonstrated that the success of inducing a fertile estrus is correlated with the day of lactation when treated, with the highest success correlated to treatment on day 25 post partum (Hodson et al. 1981), which is inconsistent with those commercial programs which wean 17–21 days after farrowing. In all cases, the success of these experimental protocols was coupled with daily or twice daily estrus detection through the period of receptivity and with multiple breedings.

I. Methods for Administration

The method for synchronizing ovulation in swine without heat detection includes the steps of administering to a swine, usually at 21 days following the time of weaning, a dose of a hormone such as a gonadotropin releasing hormone (GnRH), a luteinizing hormone (LH), a human chorionic gonadotropin (hCG), derivatives or analogues thereof, or combinations thereof, in an amount effective to stimulate ovarian follicle ovulation; and after approximately one day, breeding the sow without heat detection. Breeding may be natural or artificial.

Preferably, the swine is a postpartum sow and most preferably the hormone is administered to the sow 96 hours after weaning her piglets. In another embodiment, the swine is a postpartum sow on the first day of estrus post weaning; and hormone is administered and the swine bred without further heat detection. Alternatively, the hormone is administered at the first detectable signs of estrus.

Preferably, the sow is bred about 28 hours after the hormone is administered. A second breeding may be performed.

Pubertal gilts may have hormone administered on the first day of estrus, and be bred without further heat detection. In a preferred embodiment, the hormone is administered at the first detectable sign of estrus. In still another embodiment, the gilt is in a state of pseudopregnancy and has been administered a dose of Prostaglandin F2a. In one embodiment, the GnRH hormone is administered 48 hours after Prostaglandin F2a administration. In one embodiment, the swine was pregnant and the Prostaglandin F2a was administered for the purpose of synchronized abortion. In this embodiment, the GnRH is preferably administered 48 hours after abortion is completed.

Studies have now demonstrated that a timed injection of a single hormone such as deslorelin (GnRH analog) in SAIB excipient and timed breeding with no heat detection results in normal fertility and piglet numbers in post weaned sows. The timed injection and timed breeding abruptly curtails heat detection after the first sign of estrus is detected. A timed injection of a single hormone, deslorelin (GnRH analog), in SAIB excipient and timed breeding with no heat detection can also be used following prostaglandin PGF2a administration in gilts in a state of pseudopregnancy.

II. Compositions for Synchronization of Estrus

Hormones

The composition contains gonadotropin releasing hormone (GnRH), luteinizing hormone (LH), human chorionic gonadotropin (hCG), derivatives or analogues thereof, and combinations thereof, in an amount effective to stimulate ovarian follicle ovulation; As demonstrated in the examples, deslorelin was used at a dose of 50 mcg in SAIB administered subcutaneously near the vulva. The dosages of comparable hormones in their native form or other GnRH analogs thereof have approval for some applications in meat and dairy animals. Subject to the requirements for FDA approval, and, as will be recognized by those skilled in the art, such doses may vary since there is currently no FDA approved swine label indication.

By the term "native form" is meant the hormone having the same amino acid sequence and the same activity scale as found in nature. Thus, the native form of GnRH will include the form of the hormone, regardless of how synthesized, which is as it is produced by the hypothalamus. GnRHs which are commercially available under the trademarks Cystorelin or Factrel, are synthetic products of the same amino acid sequences and activities as naturally occurring in the animal, and are therefore considered to be the native form of the hormone. The dosage rates that are given herein are for the analog of GnRH, deslorelin, and corresponding adjustments should be made for the native forms, which have lower activity. Thus the dosage of 50 mcg of deslorelin is the dose rate for an analog of the GnRH hormone so that a native form having, as one example, one-fifth the activity would have to be dosed at a rate of 250 mcg.

Excipients

In the preferred embodiment, the hormone is suspended or dissolved in an injectable excipient. In the most preferred embodiment, this is a material such as SAIB, which is obtained from Durect under the trademark SABER™ Delivery System. This uses a high-viscosity base component, such as sucrose acetate isobutyrate (SAIB), to provide controlled release of active ingredients. After administration of a SABER™ formulation, the solvent diffuses away, leaving a viscous, adhesive matrix of the three components—SAIB, drug, and any additives. This system includes a water insoluble, high-viscosity base component, a small amount of pharmaceutically acceptable organic solvent, such as ethanol, NMP, or Miglyol® 810, to create a low-viscosity solution before application, can be administered via injection, orally, or as an aerosol, and forms an adhesive, biodegradable depot for drug delivery. These can be designed to release drug over a period of one day to three months. The more rapid delivery is desired for this application.

Other suitable excipients can also be used. BASF markets PLURONIC™ type materials, which are block copolymers based on ethylene oxide and propylene oxide. They can function as antifoaming agents, wetting agents, dispersants, thickeners, and emulsifiers. Other materials include hydrogel forming materials such as collagen, hyaluronic acid, alginate, and fibrin. Many other extended release materials and devices are also available, including various medical depo devices having similar release profiles. Other extended or sustained release formulations can be made using materials such as ion exchange resins or polymeric delivery devices.

The present invention will be further understood by reference to the following non-limiting examples.

EXAMPLE 1

Treatment with a Single Dose of Hormone Yielded Higher Litter Sizes

Figure 1B:
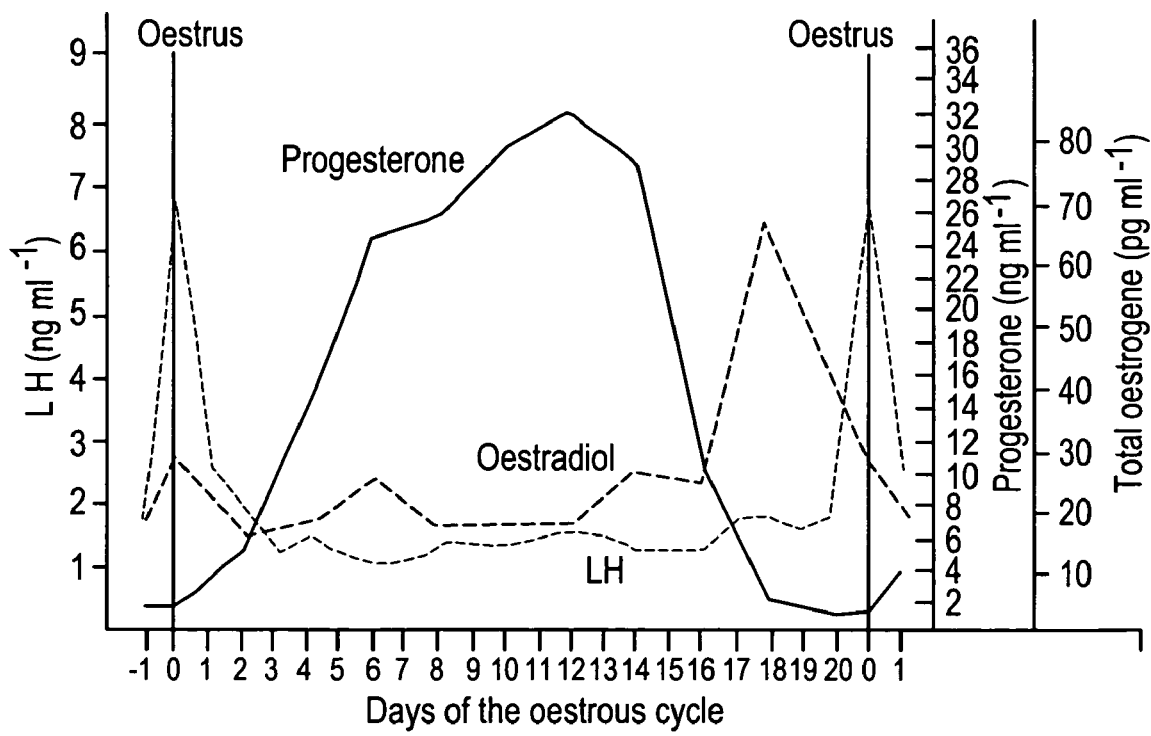

A dose response study was performed using deslorelin in SAIB in an ovariectomized estrogen primed gilt model (Barb, et al. (1999) Proceed. Int'l. Symp. Control. Rel. Bioact. Mater., 26). As shown in FIG. 1a, 50 mcg of deslorelin in SAIB produced a LH peak about twice normal value, compared to Hansel et al., (1973) Biology of Reproduction 8, 222) FIG. 1b, which returned to base level by 18 hours as determined by RIA.

EXAMPLE 2

Comparison of Intravascular Administration with Injection of Deslorelin

Based on these results a study was performed utilizing mature postpartum sows with 75 test individuals and 75 controls. Sows were assigned randomly in blocks of two to either control or to be injected intravulvar with 50 mcg of deslorelin in SAIB at the time of estrus detection for sows first detected in estrus in the a.m. and 12 hours later for those first detected in estrus in the p.m. Treated animals were bred AI upon detected estrus and again 24 hours later if still in estrus. Controls received a saline injection on first detected estrus behavior estrus detection and were bred according to the farm's normal procedures.

As shown in Table 1, there was no significant difference in pregnancy rates for sows of the Control versus Treated groups but there were 0.6 greater number of live piglets born per litter in the treated group versus control group.

TABLE 1

Estrus and Pregnancy Rates After Deslorelin Treatment In Sows

|  | Saline (Control) | Deslorelin (Treated) |
|---|---|---|
| Length of Estrus (Hrs.) | 40.74 (n = 73) | 40.81 (n = 69) |
| Pregnancy Rate | 92% (n = 75) | 91% (n = 75) |

Saline sows bred at detected estrus consistent with farm sows.
Deslorelin sows injected intravulvar with 1 ml (50 μg deslorelin acetate) at first estrus detection and AI, then AI again if in estrus the next day.
Live piglet number 0.6> in Deslorelin versus Saline sows.

EXAMPLE 3

Normal Pregnancy Rates were Attained Following Hormone Treatment in Sows

Approximately 170 postpartum sows were randomly divided into two equal groups comprised of controls and treated. Following weaning, the controls were detected for estrus and bred following the normal standard operating procedures for the farms on which they resided. The treated sows received a 50 mcg dose of deslorelin in SAIB at 96 hours post-weaning and were bred with a single insemination 28+/−2 hours later with no regard to estrus detection. The sows were examined for pregnancy by ultrasound at 21 days and slaughtered around 28 days post breeding. The entire reproductive tract was removed and corpora lutea and embryos were counted.

The data in Table 2 demonstrates that normal pregnancy rates were attained following a single timed injection of deslorelin in SAIB, at a timed interval post-weaning, followed by a single timed insemination, in the absence of any estrus (heat) detection.

TABLE 2

Pregnancy Rates and Embryo Numbers After Deslorelin Treatment in Sows

|  | Number In Group | Sows Pregnant | Live Embryos | CL | Embryo Survival | Pregnancy Rate |
|---|---|---|---|---|---|---|
| Controls | 82 | 54 | 13.6 | 20.2 | 68% | 66% |
| Treated | 84 | 60 | 13.4 | 20.9 | 64% | 71% |

EXAMPLE 4

Normal Litter Sizes and Pregnancy Rates were Attained Following Hormone Treatment in Sows Postpartum sows were randomly distributed into three different groups comprised of Controls, Treatment 1, and Treatment 2, with the exception of Site 3, which was divided into two groups, Control and Treatment 2. Control sows were detected for estrus following weaning, and bred following the normal standard operating procedures for the farms on which they resided. Treatment 1 sows were detected for estrus following weaning, and received a 50 mcg dose of deslorelin in the morning when standing and were bred by AI 4 hours later and again at 24+/−2 hours later. Treatment 2 sows received a 50 mcg dose of deslorelin in SAIB at 96 or 120 hours post-weaning and were bred with a single insemination 28+/−2 hours later with no regard to estrus detection.

As shown in Table 3, Table 4, and Table 5 deslorelin treatment resulted in normal litter sizes in sows regardless of estrus detection.

TABLE 3

Litter Size After Deslorelin Treatment in Sows Site 1

|  | Number in Group | Avg. Total Pigs Born | Avg. Total Live Pigs |
|---|---|---|---|
| Controls | 38 | 12.74 | 11.35 |
| Treatment 1 | 39 | 12.10 | 11.03 |
| Treatment 2 | 40 | 12.37 | 11.24 |

TABLE 4

Litter Size After Deslorelin Treatment in Sows Site 2

|  | Number in Group | Avg. Total Pigs Born | Avg. Total Live Pigs |
|---|---|---|---|
| Controls | 68 | 11.23 | 10.57 |
| Treatment 1 | 72 | 11.21 | 10.25 |
| Treatment 2 | 66 | 10.88 | 10.02 |

TABLE 5

Litter Size After Deslorelin Treatment in Sows Site 3

|  | Number in Group | Avg. Total Pigs Born | Avg. Total Live Pigs |
|---|---|---|---|
| Controls | 58 | 11.26 | 10.58 |
| Treatment 2 | 60 | 11.09 | 10.27 |

As shown in Table 6, normal pregnancy rates were obtained following deslorelin treatment in sows.

Table 3, Table 4, and Table 5 demonstrate that normal litter sizes were attained following treatment with a single dose of deslorelin in SAIB in postpartum sows. Table 3, Table 4, and Table 5 represent data obtained from three different farm sites. Table 6 summarizes the data from Table 2, Table 3, Table 4, and Table 5, and demonstrates that normal pregnancy rates were obtained following deslorelin treatment in sows. Significantly, these results demonstrate that the same number of pigs can be obtained with the least amount of labor.

TABLE 6

Pregnancy Rate After Deslorelin Treatment in Sows

|  | Number in Group | Number Pregnant | % Pregnant |
|---|---|---|---|
| Controls | 246 | 172 | 69.92% |
| Treatment 2 | 250 | 177 | 70.80% |

It will be understood that modifications thereof may be suggested to those skilled in the art, and it is intended to cover all such modifications as fall within the scope of appended claims.

What is claimed:

1. A method consisting essentially of:
   (a) synchronizing time of insemination in a swine without heat detection by administering to a swine a dose of a hormone selected from the group consisting of a gonadotropin releasing hormone (GnRH), a luteinizing hormone (LH), a human chorionic gonadotropin (hCG), derivatives and analogues thereof, and combinations thereof, in an amount effective to stimulate ovarian follicle ovulation; and
   (b) breeding the swine,
   wherein the swine is a postpartum sow and the hormone is administered to the sow on the first day of estrus postweaning, 96 hours after weaning her piglets or 120 hours after weaning her piglets, or wherein the swine is a pubertal gilt and the hormone is administered on the first day of estrus, and steps (a) and (b) are performed without further heat detection.

2. The method of claim 1, wherein the swine is a postpartum sow.

3. The method of claim 2, wherein the sow is bred about 28 hours after the hormone is administered.

4. The method of claim 2, wherein the hormone is administered to a sow 96 hours or 120 hours after weaning her piglets.

5. The method of claim 2, wherein a second breeding is performed subsequent to the breeding in 1(b).

6. The method of claim 1, wherein the swine is a postpartum sow and the hormone is administered on the first day of estrus postweaning; and steps (a) and (b) are performed without further heat detection.

7. The method of claim 6, wherein a second breeding is performed subsequent to the breeding in 1(b).

8. The method of claim 1, wherein the swine is a pubertal gilt and the hormone is administered on the first day of estrus, and steps (a) and (b) are performed without further heat detection.

9. The method of claim 8, wherein a second breeding is performed subsequent to the breeding in 1(b).

10. The method of claim 1, wherein the swine is a gilt in a state of pseudopregnancy and has been administered a dose of Prostaglandin F2a.

11. The method of claim 10, wherein the hormone is administered 48 hours after Prostaglandin F2a administration.

12. The method of claim 10, wherein a second breeding is performed subsequent to the breeding in 1(b).

13. The method of claim 1, wherein the swine is a gilt in a state of pregnancy and has been administered Prostaglandin F2a for the purpose of synchronized abortion.

14. The method of claim 13, wherein the hormone is administered 48 hours after abortion is completed.

15. The method of claim 13, wherein a second breeding is performed subsequent to be breeding in 1(b).

* * * * *